(12) United States Patent
Torfs (10) Patent No.: US 10,420,511 B2
(45) Date of Patent: Sep. 24, 2019

(54) SYSTEM AND METHOD FOR ACQUISITION OF BIOSIGNALS WITH MOTION SENSOR-BASED ARTIFACT COMPENSATION

(71) Applicant: IMEC VZW, Leuven (BE)

(72) Inventor: Tom Torfs, Kraainem (BE)

(73) Assignee: IMEC VZW, Leuven (BE)

( * ) Notice: Subject to any disclaimer, the term of this patent is extended or adjusted under 35 U.S.C. 154(b) by 346 days.

(21) Appl. No.: 15/381,923

(22) Filed: Dec. 16, 2016

(65) Prior Publication Data
US 2017/0172511 A1    Jun. 22, 2017

(30) Foreign Application Priority Data

Dec. 22, 2015    (EP) .................................... 15202064

(51) Int. Cl.
    *A61B 5/00*        (2006.01)
    *G01C 19/5776*     (2012.01)
    *G01C 21/12*       (2006.01)

(52) U.S. Cl.
    CPC .............. *A61B 5/721* (2013.01); *G01C 21/12* (2013.01); *A61B 5/6802* (2013.01); *A61B 5/725* (2013.01); *A61B 2562/04* (2013.01)

(58) Field of Classification Search
    CPC ...... A61B 2562/04; A61B 5/721; G01C 21/12
    USPC ...... 73/1.38, 488, 510; 702/19, 94, 141, 150
    See application file for complete search history.

(56) References Cited

U.S. PATENT DOCUMENTS

| 5,513,649 | A  |   | 5/1996  | Gevins et al. |
| 9,785,247 | B1 | * | 10/2017 | Horowitz ................ G06F 3/017 |
| 2008/0208028 | A1 |  | 8/2008  | Thijs et al. |
| 2012/0143020 | A1 |  | 6/2012  | Bordoley et al. |

(Continued)

FOREIGN PATENT DOCUMENTS

EP        2 792 297 A1    10/2014

OTHER PUBLICATIONS

Tsai, Yi-Lung et al., "EcoIMU: A Dual Triaxial-Accelerometer Inertial Measurement Unit for Wearable Applications", 2010 International Conference on Body Sensor Networks, 2010, pp. 207-212.

*Primary Examiner* — John E Breene
*Assistant Examiner* — Jeffrey P Aiello
(74) *Attorney, Agent, or Firm* — McDonnell Boehnen Hulbert & Berghoff LLP (57) ABSTRACT

The disclosure relates to systems and methods for acquisition of biosignals with motion sensor-based artifact compensation. One example embodiment is a system for acquisition of biosignals from a subject. The system includes at least one biosensor worn over a first location of a body part of the subject configured for biosignal measurement and providing a measured biosignal. The system also includes a plurality of inertial motion sensors worn over a plurality of locations of the body part of the subject. Each of the inertial motion sensors is configured for providing a motion vector signal. The system further includes a biosignal adaptation unit configured for receiving and adapting the measured biosignal. In addition, the system includes a motion estimation unit. Further, the system includes a digital filter unit. At least one of the plurality of inertial motion sensors is mechanically connected to the at least one biosensor.

20 Claims, 4 Drawing Sheets

(56) References Cited

U.S. PATENT DOCUMENTS

| | | | |
|---|---|---|---|
| 2013/0178958 A1* | 7/2013 | Kulach | A63B 24/0021 700/91 |
| 2014/0135960 A1* | 5/2014 | Choi | A61B 5/0205 700/91 |
| 2014/0142485 A1* | 5/2014 | Berry | A61F 5/028 602/19 |
| 2014/0318699 A1* | 10/2014 | Longinotti-Buitoni | A61B 5/0002 156/247 |
| 2015/0208954 A1* | 7/2015 | Kim | A61B 5/1114 600/595 |
| 2016/0030809 A1* | 2/2016 | Wisbey | A61B 5/02405 600/301 |
| 2016/0367188 A1* | 12/2016 | Malik | A61B 5/682 |
| 2017/0003747 A1* | 1/2017 | Carceroni | G06F 3/017 |
| 2017/0120107 A1* | 5/2017 | Wisbey | G09B 19/00 |
| 2017/0251295 A1* | 8/2017 | Pergament | A61B 5/4809 |

\* cited by examiner

FIG. 4

SYSTEM AND METHOD FOR ACQUISITION OF BIOSIGNALS WITH MOTION SENSOR-BASED ARTIFACT COMPENSATION

CROSS-REFERENCE TO RELATED APPLICATIONS

The present application is a non-provisional patent application claiming priority to European Patent Application No. EP 15202064.0, filed Dec. 22, 2015, the contents of which are hereby incorporated by reference.

FIELD OF THE DISCLOSURE

The present disclosure relates to the field of systems and methods for biosignal acquisition and more specifically to a system and a method for acquisition of biosignals using motion artifact removal techniques.

BACKGROUND

Sensors and sensor modules worn on the body to measure or monitor biosignals, such as for example electrocardiogram (ECG), electroencephalogram (EEG), electromyogram (EMG), bioimpedance or photoplethysmogram (PPG) signals, frequently suffer from artifacts caused by motion of the body, especially when the sensors are intended to operate in continuous or ambulatory mode. A key technical challenge in such application environments is overcoming motion artifacts that significantly affect the measurements when the body is moving.

Patent application EP 2 792 297 A1, for example, describes a system for the analysis of biopotential signals, comprising a motion classification module configured for determining motion information comprising the type and/or severity of the motion phenomena causing artifacts in the biopotential signal and communicating the motion information to a motion artifact reduction module, which will perform motion artifact removal from the biopotential signal based on the information received from the motion classification module. The motion classification module receives one or more secondary inputs related to the subject or electrode motion and/or direct or indirect artifact distortion, where the secondary inputs being, for example, electrode-to-tissue impedance, applied or contact force or acceleration of/on the electrode.

U.S. Pat. No. 5,513,649 also describes a system to detect brain waves from a subject, wherein the adverse effect on the EEG recording of artifacts due to head, body and eye movements is reduced. A reference signal of the movement contaminating the EEG signals is provided by one or more of several alternatives, including an accelerometer or other type of motion detector, and spatial averages of the EEG channels. For example, an accelerometer or a motion detector detects head motion and determines the starting and ending of movement artifact and the spatial average EEG signal is the reference signal which is used only during such movement artifact. An adaptive digital filter removes the contaminants caused by the head, body and eye movements to produce corrected and usable EEG signals.

Also, U.S. Patent Application No. 2008/0208028 and U.S. Patent Application No. 2012/0143020 describe systems for the analysis of biopotential signals in which further motion artifact reduction or motion artifact handling techniques are used.

There is a motivation to improve current systems for the analysis of biosignals in order to obtain better motion artifact reduction.

SUMMARY

The present disclosure describes a biosignal acquisition system with improved motion artifact reduction.

The scope of the invention is defined by the claims.

According to one example embodiment, the proposed system reduces the severity of motion artifacts through the use of a plurality of motion sensors.

According to an example embodiment, there is provided a system for acquisition of biosignals from a subject, comprising: at least one biosensor worn over a first location of a subject's body part and configured for biosignal measurement and providing a measured biosignal; a plurality of inertial motion sensors worn over a plurality of locations of the subject's body part and configured for motion vector measurement and each providing a motion vector signal; a biosignal adaptation unit configured for receiving the measured biosignal and adapting it into a digital measured biosignal; a motion estimation unit configured for receiving the motion vector signals from the plurality of inertial motion sensors and calculating a digital reference motion signal; a digital filter unit configured for receiving the digital measured biosignal and the digital reference motion signal and performing removal of motion artifacts affecting the digital measured biosignal; wherein at least one of the plurality of inertial motion sensors is mechanically connected to the at least one biosensor worn over the first location of the subject's body part; and the digital reference motion signal is a relative motion vector signal indicating the relative motion of the at least one biosensor with respect to the first location of the subject's body part.

The system according to an example embodiment calculates and uses the relative motion between the inertial motion sensors associated to a biosensor and the body as a reference signal, which is correlated to the motion artifact, to electronically correct (remove or reduce) the motion artifact. Example embodiments may be used with non-contact or loose-contact biosignal measurement electrodes and motion sensors, for example dry electrodes and sensors integrated into clothing. Even when used with contact electrodes, example embodiments provide improved robustness.

According to an example embodiment, the relative motion vector signal is calculated by first calculating, with the received motion vector signals, an average motion vector of the subject's body part; and then performing a vectorial subtraction of the inertial motion sensor's motion vector mechanically connected to the at least one biosensor and the calculated average motion vector. According to an example embodiment, the received motion vector signals are absolute motion vector signals and the average motion vector of the subject's body part is an average absolute motion vector of the subject's body part.

According to an example embodiment, the system further comprises a second biosensor worn over a second location of a subject's body part and providing a second measured biosignal; and a second inertial motion sensor mechanically connected to the second biosensor; wherein the motion estimation unit is configured to further calculate a digital reference motion signal which is a relative motion vector signal indicating the relative motion of the second biosensor with respect to a second location of the subject's body part; and wherein the digital filter unit is configured for calculating a digital filtered version without and/or reduced motion artifact of the second measured biosignal.

The description also relates to a method for acquisition of biosignals from a subject comprising: receiving a measured biosignal from at least one biosensor worn over a first location of a subject's body part; receiving a plurality of motion vector signals from a plurality of inertial motion sensors worn over a plurality of locations of the subject's body part, wherein at least one of the plurality of inertial motion sensors is mechanically connected to the at least one biosensor worn over the first location of the subject's body part; calculating a reference motion signal from the received plurality of motion vector signals, wherein the reference motion signal is a relative motion vector signal indicating the relative motion of the at least one biosensor with respect to the first location of the subject's body part; and performing removal of motion artifacts affecting the measured biosignal. The biosignals and motion vector signals may be for example transmitted wirelessly to an electronic device or computer network communicatively connected to the biosensors and inertial motion sensors.

According to an example embodiment, the relative motion vector signal is calculated by first calculating, with the received motion vector signals, an average motion vector of the subject's body part; and then performing a vectorial subtraction of the inertial motion sensor's motion vector mechanically connected to the at least one biosensor and the calculated average motion vector.

The description also relates to a computer program product comprising computer program code adapted for acquisition of biosignals from a subject according to example methods of the present description, when the program is run on a hardware with processing capabilities such as a microprocessor or microcontroller. The description also relates to a computer readable storage medium comprising a computer program.

The description also relates to an electronic device or body wearable item (such as a piece of clothing or wearable element) comprising a biosignal acquisition system and/or a computer program product and/or a computer readable storage medium according to embodiments described in the claims.

The description also relates to a computer network comprising a computer program product and/or a computer readable storage medium according to embodiments described in the claims.

Certain objects of various aspects have been described above. It is to be understood that not necessarily all such objects may be achieved in accordance with any particular embodiment of the present disclosure as described in the claims. Those skilled in the art will recognize that the claims may be embodied or carried out in various manners.

BRIEF DESCRIPTION OF THE FIGURES

The above and other aspects of the system and method for acquisition of biosignals will be shown and explained with reference to the non-restrictive example embodiments described hereinafter.

DETAILED DESCRIPTION

In the following, in the description of example embodiments, various features may be grouped together in a single embodiment, figure, or description thereof for the purpose of streamlining the disclosure and aiding in the understanding of one or more of the various disclosed aspects. This is however not to be interpreted as certain embodiments requiring more features than the ones expressly recited in the independent claims. Furthermore, combinations of features of different embodiments and obvious known alternative structures are meant to be within the scope of the present description, as would be clearly understood and derived by those skilled in the art. Additionally, in some examples, well-known methods, structures and techniques have not been shown in detail in order not to obscure the conciseness of the description.

Figure 1:
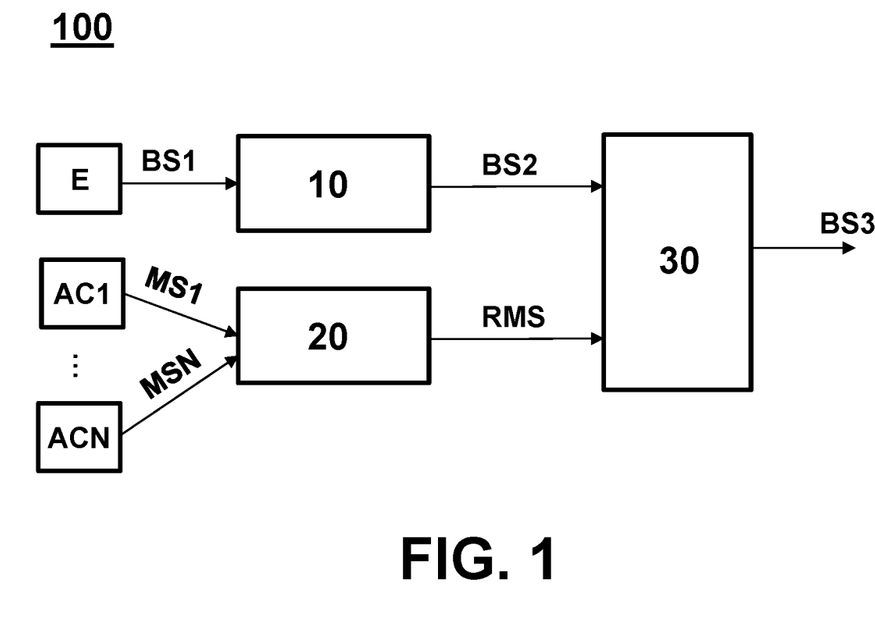
FIG. 1 shows a first block diagram of a system for acquisition of biosignals, according to example embodiments.

FIG. 1 shows an example schematic block diagram of a system 100 for acquisition of biosignals, comprising at least one biosensor or biosignal measurement electrode E, a biosignal adaptation unit 10, a plurality of inertial motion sensors AC1 to ACN, a motion estimation unit 20 and a digital filter unit 30.

According to an example embodiment, the biosignal adaptation unit 10 is configured for receiving at least one measured biosignal BS1, which may be acquired, for example, from at least one biosensor E attached to or worn over a living being body part, and further for adapting such measured biosignal BS1 into a digital biosignal BS2 suitable for being received by the digital filtering unit 30. The biosignal adaptation unit 10 may comprise for example, signal amplification, filtering and/or an analog-to-digital converter.

According to an example embodiment, the plurality of inertial motion sensors AC1 to ACN are attached to or are worn over the body. A first plurality of the inertial motion sensors AC1 to ACN may be physically integrated in the same sensing unit or module as other biosensors E and a second plurality may also be implemented as independent units located in different parts of the body. Each of the inertial motion sensors may measure a motion vector for that module location. The inertial motion sensor may be an accelerometer, a gyroscope, a magnetometer or a combination thereof and/or other sensors that may improve the motion sensing capabilities. The inertial motion sensor may continuously or periodically measure the motion vector of the sensor.

According to an example embodiment, the motion estimation unit 20 is configured for receiving the plurality of motion vector signals MS1 to MSN from the plurality of inertial motion sensors AC1 to ACN and calculating a reference relative motion signal RMS. The reference relative motion signal RMS comprises a relative motion vector estimation for each inertial motion sensor with respect to the body or a body part. The relative motion vector may be calculated for example by first calculating an average motion vector yielding an estimate of a motion vector of the body or body part followed by a vectorial subtraction of the inertial motion sensor's motion vector associated to a biosensor and the calculated average motion vector (determining the relative motion of the biosensor with respect to the average motion vector of the body or body part). According to an embodiment, each biosensor E, for which the relative motion vector is to be estimated, is mechanically connected to an inertial motion sensor of the plurality of inertial motion sensors AC1 to ACN, e.g. the biosensor and the inertial motion sensor may be located in the same sensor module. The system 100 may comprise additional inertial motion sensors worn elsewhere on the body or body part, not mechanically connected to a specific biosensor, to allow improve the estimate of the average motion vector of the body or body part.

According to an example embodiment, the digital filter unit 30 is configured for receiving the digital adapted versions of the measured biosignal BS2 and the reference relative motion signal RMS and for performing motion artifact reduction on such digital adapted version of the measured biosignal BS2. According to some embodiments, the reference relative motion signal RMS is at least partially correlated to the motion artifacts, caused by relative body motion, that affect the measured biosignal BS1. The reference relative motion signal RMS is then used by the digital filter unit 30 as a reference signal input to reduce the severity of the motion artifacts in the digital adapted version of the measured biosignal BS2 and improve the signal to noise ratio. The digital filter unit 30 generates a digital filtered version of the measured biosignal BS3 which is an estimation of the measured biosignal BS1 without and/or reduced motion artifacts. The digital filter unit 30 uses signal processing algorithms for removal or reduction of body motion artifacts and may be implemented using known adaptive filtering techniques known in the art or using ICA analysis techniques. Obtaining an estimate of the relative motion of the sensors permits a much better correlation of the reference signal with the motion artifacts and enables signal processing algorithm techniques like adaptive filtering to have a superior performance in reducing the motion artifacts in the biosignals.

It shall be understood that the described elements of the system 100 for acquisition of biosignals may not be integrated in the same physical module and location. For example, the at least one electrode E and the plurality of inertial motion sensors AC1 to ACN may be individual devices and/or integrated in wearable devices and/or body garments and located in different parts on the body, although it is understood that for each biosensor E, for which a relative motion vector is to be estimated, an inertial motion sensor shall be located in the same location and be mechanically connected to that biosensor. In the same sense, the biosignal adaptation unit 10, the motion estimation unit 20 and the digital filter unit 30 may be located in the same or different device (e.g., a smartphone and/or a wearable device). The elements of the system 100 for acquisition of biosignals may communicate wirelessly, or using hardwires, with each other. It shall also be noted that the biosignal adaptation unit 10, the motion estimation unit 20 and the digital filter unit 30 according to certain embodiments may be implemented according to hardware and/or software state of the art techniques, and such units may comprise for example a microprocessor, microcontroller or digital signal processor that can understand and execute software program instructions. Some programmable hardware logic and memory may be specifically designed also for executing the method or parts of it according to example embodiments.

Figure 2:
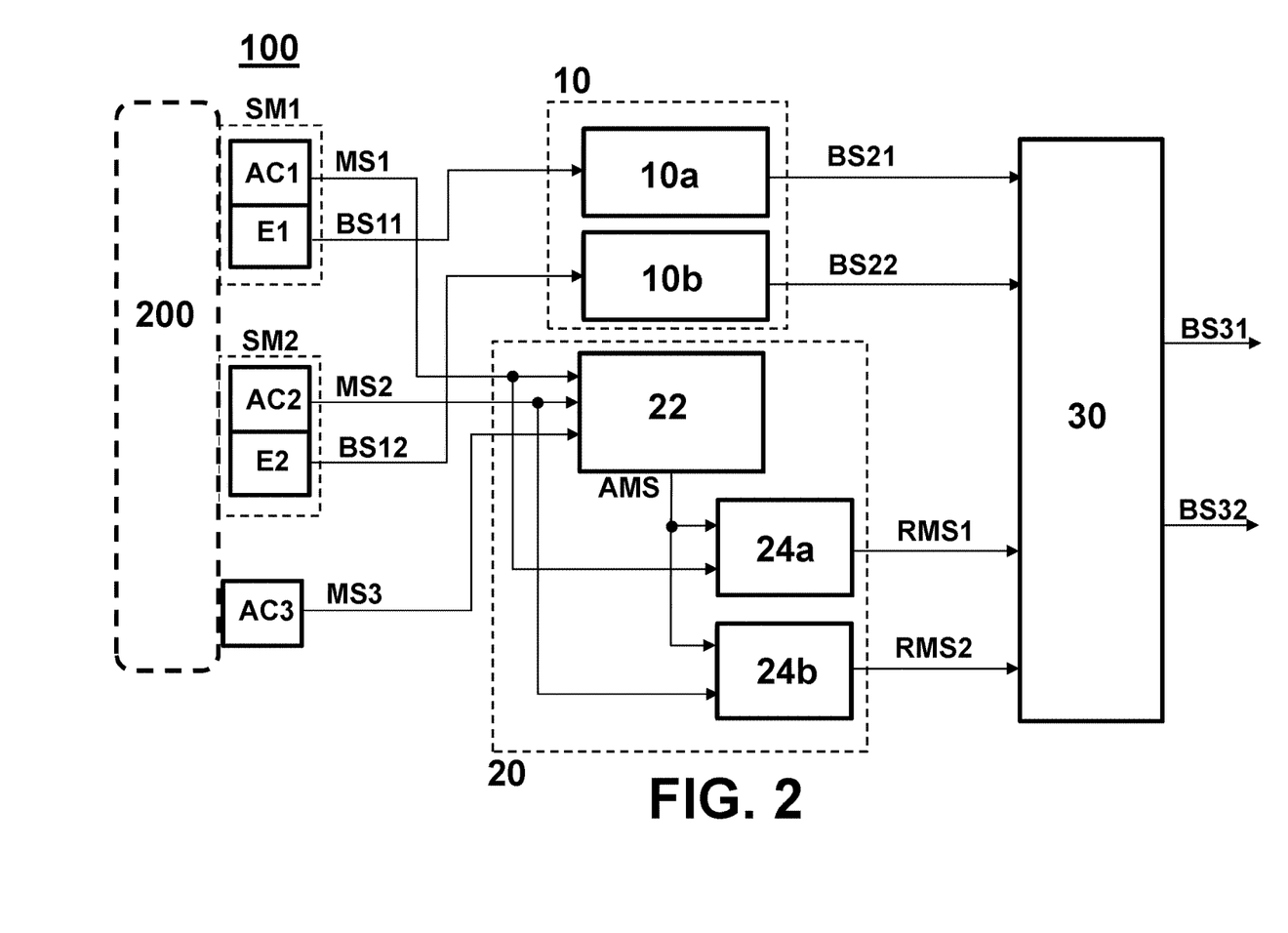
FIG. 2 shows a second block diagram of a system for acquisition of biosignals, according to example embodiments.

FIG. 2 shows a shows a second example block diagram of a system 100 for acquisition of biosignals, comprising two biosensors E1, E2 and three inertial motion sensors AC1, AC2, AC3. A first and a second biosensor E1, E2 are mechanically coupled to a first and a second inertial motion sensor AC1, AC2 respectively, forming a first and a second sensor module SM1, SM2. The first and second motion sensor modules SM1, SM2 and the third inertial motion sensor AC3 are attached or fixed to the body 200, or specifically a body part, of a living being. Biosensors E1, E2 generate biosignals BS11, BS12 sensed on the locations of the body of the living being to which they are attached. The measured biosignals BS11, BS12 may be corrupted with motion artifacts due to movements of the body, body part and/or sensor module and may be pre-processed in a biosignal adaptation unit 10. The biosignal adaptation unit 10 may comprise modules 10a, 10b for, among other, analog-to-digital conversion, gain control or adjustment, filtering and/or differential amplification processing. Inertial motion sensors AC1, AC2, AC3 generate absolute motion vector signals MS1, MS2, MS3 sensed on the locations of the body of the living being to which they are attached and are input to a vectorial average module 22 which calculates and generates an average absolute motion vector signal AMS of the body or body part. The average absolute motion vector signal AMS from the vectorial average module 22 and the absolute motion vector signals MS1, MS2 from the sensor modules SM1, SM2 are then input to vectorial subtraction modules 24a, 24b which calculate a relative motion vector RMS1, RMS2 of the first and second sensor module SM1, SM2 respectively, to the body or body part. The digital filter unit 30 then receives the relative motion vector RMS1, RMS2 and the measured biosignals BS11, BS12 or digitally pre-processed biosignals BS21, BS22 and calculates a digital filtered version BS31, BS32 of the measured biosignals, which is an estimation of the measured biosignal BS11, BS12 respectively, without and/or reduced motion artifacts. The digital filter unit 30 may also use the information about the relative motion vector RMS2 of the second sensor module SM2 for calculating the digital filtered version BS31 without and/or reduced motion artifact of the first measured biosignal BS11. In the same way, the digital filter unit 30 may also use the information about the relative motion vector RMS1 of the first sensor module SM1 for calculating the digital filtered version BS32 without and/or reduced motion artifact of the second measured biosignal BS12. The digital filter unit 30 may be implemented with state of the art software and/or hardware digital filtering techniques. Although some of the modules of the biosignal adaptation unit 10 and the motion estimation unit 20 in this figure have been illustrated in different parallel software and or hardware instantiations, it is understood that they can be implemented also in sequential form and vice versa, that is, modules that have been illustrated as unique, single instantiations can also be implemented or split in further parallel calculation modules.

According to an example embodiment, in order to calculate a relative motion vector RMS1, RMS2 indicating the relative motion of each biosensor E1, E2 respectively, with respect to a body or body part 200, the sensor modules SM1, SM2 that include the biosensors E1, E2 respectively, also include an inertial motion sensor AC1, AC2 mechanically coupled to the biosensor. The additional inertial motion sensor AC3 (not mechanically connected to a biosensor) is used to improve the estimate of the average motion vector of the body or body part.

Figure 3:
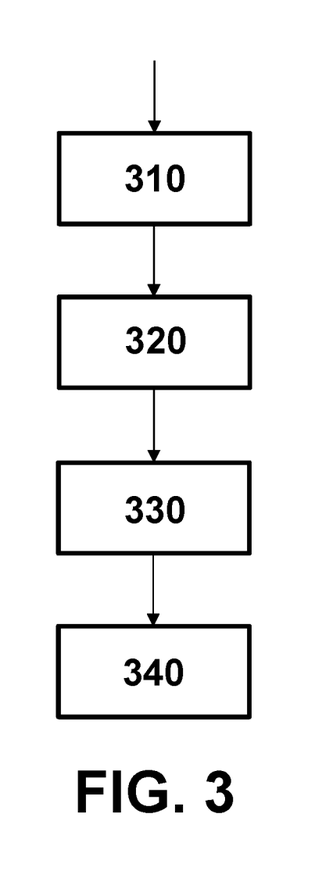
FIG. 3 illustrates a flow diagram of an method for acquisition of biosignals, according to example embodiments.

FIG. 3 illustrates a flow diagram of an example method for acquisition of biosignals. The method comprises, in a first step 310, receiving a measured biosignal from a first biosensor fixed or attached to a first location of a subject's body or body part and receiving a plurality of absolute motion vector signals from a plurality of inertial motion sensors fixed or attached to a plurality of locations of the subject's body or body part, wherein at least one of the plurality of inertial motion sensors is mechanically connected to the first biosensor; in a second step 320, calculating an average absolute motion vector corresponding to the body or body part; in a third step 330, calculating a relative motion vector of the first biosensor to the body or body part, by e.g. performing a vectorial subtraction between the absolute motion vector of the inertial motion sensor mechanically connected to the first biosensor and the average absolute motion vector; and, in a fourth step 340, performing removal of motion artifacts affecting the measured biosignal using the calculated relative motion vector of the first biosensor to the body or body part.

Figure 4:
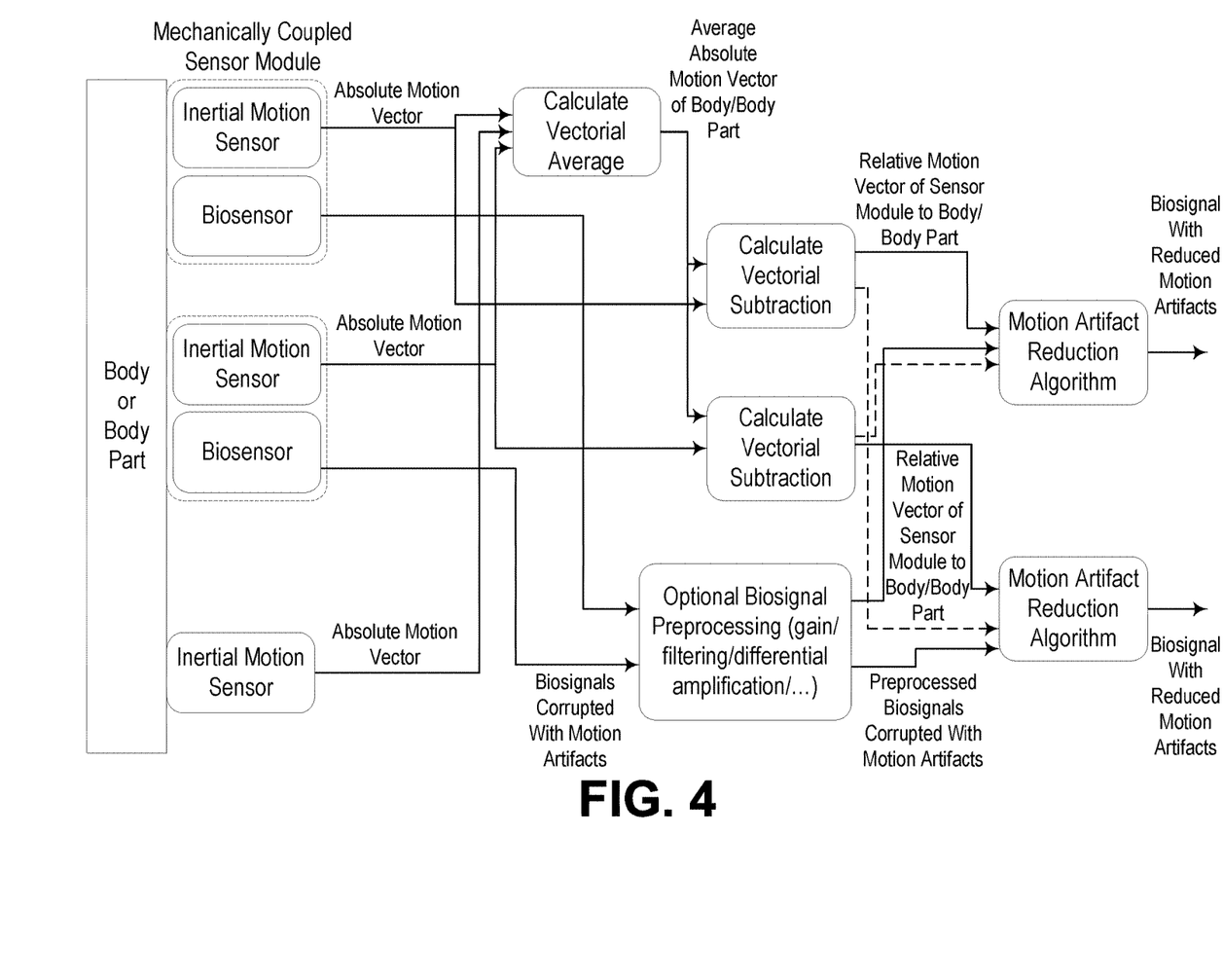
FIG. 4 shows a third block diagram of a system for acquisition of biosignals, according to example embodiments.

FIG. 4 shows a third example block diagram of a system for acquisition of biosignals, comprising two biosensors and three inertial motion sensors. In order to calculate a relative motion vector indicating the relative motion of each biosensor with respect to a body or body part, the sensor modules that include the biosensors also include an inertial motion sensor mechanically coupled to the biosensor. The additional inertial motion sensor (not mechanically connected to a biosensor) is used to improve the estimate of the average motion vector of the body or body part.

A motion artifact reduction algorithm is used to remove or reduce the motion artifacts from the measured biosignals using the calculated relative motion vector of the biosensor (or sensor module). According to an example embodiment, the motion artifact reduction algorithm may also use or combine the information from two or more relative motion vectors calculated for two or more biosensors (or sensor modules) in order to reduce the motion artifact.

It shall be understood that FIG. 4 is just for illustration purposes and only shows two sensor modules with a biosensor and one standalone inertial motion sensor, but the concept can be applied to any plurality (at least two) of sensor modules.

What is claimed is:

1. A system for acquisition of biosignals from a subject, comprising:
   at least one biosensor worn over a first location of a body part of the subject and configured for biosignal measurement and providing a measured biosignal;
   a plurality of inertial motion sensors worn over a plurality of locations of the body part of the subject, wherein the plurality of inertial motion sensors is configured for motion vector measurement, and wherein each inertial motion sensor is configured for providing a motion vector signal;
   a biosignal adaptation unit configured for receiving the measured biosignal and adapting the measured biosignal into a digital measured biosignal;
   a motion estimation unit configured for receiving the motion vector signals from the plurality of inertial motion sensors and calculating a digital reference motion signal; and
   a digital filter unit configured for receiving the digital measured biosignal and the digital reference motion signal and performing removal of motion artifacts affecting the digital measured biosignal,
   wherein at least one of the plurality of inertial motion sensors is mechanically connected to the at least one biosensor,
   wherein the digital reference motion signal comprises a relative motion vector signal indicating relative motion of the at least one biosensor with respect to the first location of the body part of the subject, and
   wherein the relative motion vector signal is calculated by:
      calculating, with the received motion vector signals, an average motion vector of the body part of the subject; and
      performing a vectorial subtraction between (i) the motion vector signal of the inertial motion sensor that is mechanically connected to the at least one biosensor and (ii) the calculated average motion vector.

2. The system according to claim 1, wherein at least one of the plurality of inertial motion sensors is not mechanically connected to the at least one biosensor.

3. The system according to claim 1, wherein the received motion vector signals comprise absolute motion vector signals and the average motion vector of the body part of the subject comprises an average absolute motion vector of the body part of the subject.

4. The system according to claim 1, further comprising:
   a second biosensor worn over a second location of the body part of the subject and configured for providing a second measured biosignal; and
   a second inertial motion sensor mechanically connected to the second biosensor,
   wherein the motion estimation unit is further configured to calculate a second digital reference motion signal,
   wherein the second digital reference motion signal comprises a relative motion vector signal indicating relative motion of the second biosensor with respect to the second location of the body part of the subject,
   wherein the digital filter unit is further configured for calculating a digital filtered version of the second measured biosignal, and
   wherein the digital filtered version of the second measured biosignal has reduced motion artifacts and/or does not have motion artifacts.

5. The system according to claim 1, wherein the system is a component of an electronic device for acquisition of biosignals from the subject.

6. The system according to claim 1, wherein the system is a component of a body-wearable item for acquisition of biosignals from the subject.

7. The system according to claim 1, wherein the plurality of inertial motion sensors comprises an accelerometer, a gyroscope, or a magnetometer.

8. A method for acquisition of biosignals from a subject, comprising:
   receiving a measured biosignal from at least one biosensor worn over a first location of a body part of the subject;
   receiving a plurality of motion vector signals from a plurality of inertial motion sensors worn over a plurality of locations of the body part of the subject;
   calculating a reference motion signal from the received plurality of motion vector signals; and
   performing removal of motion artifacts affecting the measured biosignal,
   wherein at least one of the plurality of inertial motion sensors is mechanically connected to the at least one biosensor,
   wherein the reference motion signal comprises a relative motion vector signal indicating relative motion of the at least one biosensor with respect to the first location of the body part of the subject, and
   wherein calculating the relative motion vector signal comprises:

calculating, with the received motion vector signals, an average motion vector of the body part of the subject; and performing a vectorial subtraction between (i) the motion vector signal of the inertial motion sensor that is mechanically connected to the at least one biosensor and (ii) the calculated average motion vector.

9. The method according to claim 8, wherein at least one of the plurality of inertial motion sensors is not mechanically connected to the at least one biosensor.

10. The method according to claim 8, wherein the received plurality of motion vector signals comprise absolute motion vector signals, and wherein the average motion vector of the body part of the subject comprises an average absolute motion vector of the body part of the subject.

11. The method according to claim 8, further comprising:
receiving a second measured biosignal from a second biosensor worn over a second location of the body part of the subject, wherein a second inertial motion sensor is mechanically connected to the second biosensor;
calculating a second digital reference motion signal, wherein the second digital reference motion signal comprises a relative motion vector signal indicating relative motion of the second biosensor with respect to the second location of the body part of the subject; and
calculating a digital filtered version of the second measured biosignal, wherein the digital filtered version of the second measured biosignal has reduced motion artifacts or does not have motion artifacts.

12. The method according to claim 8, wherein the plurality of inertial motion sensors comprises an accelerometer, a gyroscope, or a magnetometer.

13. A non-transitory computer-readable storage medium comprising software program instructions stored thereon, wherein the software program instructions are executable by a microprocessor to perform a method for acquisition of biosignals from a subject, comprising:
receiving a measured biosignal from at least one biosensor worn over a first location of a body part of the subject;
receiving a plurality of motion vector signals from a plurality of inertial motion sensors worn over a plurality of locations of the body part of the subject;
calculating a reference motion signal from the received plurality of motion vector signals; and
performing removal of motion artifacts affecting the measured biosignal,
wherein at least one of the plurality of inertial motion sensors is mechanically connected to the at least one biosensor,
wherein the reference motion signal comprises a relative motion vector signal indicating relative motion of the at least one biosensor with respect to the first location of the body part of the subject, and wherein calculating the relative motion vector signal comprises:
calculating, with the received motion vector signals, an average motion vector of the body part of the subject; and
performing a vectorial subtraction between (i) the motion vector signal of the inertial motion sensor that is mechanically connected to the at least one biosensor and (ii) the calculated average motion vector.

14. The non-transitory computer-readable storage medium according to claim 13, wherein at least one of the plurality of inertial motion sensors is not mechanically connected to the at least one biosensor.

15. The non-transitory computer-readable storage medium according to claim 13, wherein the received plurality of motion vector signals comprise absolute motion vector signals and the average motion vector of the body part of the subject comprises an average absolute motion vector of the body part of the subject.

16. The non-transitory computer-readable storage medium according to claim 13, further comprising:
receiving a second measured biosignal from a second biosensor worn over a second location of the body part of the subject, wherein a second inertial motion sensor is mechanically connected to the second biosensor;
calculating a second digital reference motion signal, wherein the second digital reference motion signal comprises a relative motion vector signal indicating relative motion of the second biosensor with respect to the second location of the body part of the subject; and
calculating a digital filtered version of the second measured biosignal, wherein the digital filtered version of the second measured biosignal has reduced motion artifacts or does not have motion artifacts.

17. The non-transitory computer-readable storage medium according to claim 13, wherein the non-transitory computer-readable storage medium is a component of an electronic device for acquisition of biosignals from the subject.

18. The non-transitory computer-readable storage medium according to claim 13, wherein the non-transitory computer-readable storage medium is a component of a body-wearable item for acquisition of biosignals from the subject.

19. The non-transitory computer-readable storage medium according to claim 13, wherein the non-transitory computer-readable storage medium is a component of a computer network.

20. The non-transitory computer-readable storage medium according to claim 13, wherein the plurality of inertial motion sensors comprises an accelerometer, a gyroscope, or a magnetometer.

* * * * *